(12) United States Patent
Merk

(10) Patent No.: US 11,959,059 B2
(45) Date of Patent: Apr. 16, 2024

(54) INCUBATOR WITH ORBITAL SHAKER

(71) Applicant: DAMECX UG (haftungsbeschränkt), Meerbusch (DE)

(72) Inventor: Winfried Merk, Karlsbad (DE)

(73) Assignee: DAMECX UG (HAFTUNGSBESCHRÄNKT), Meerbusch (DE)

( * ) Notice: Subject to any disclaimer, the term of this patent is extended or adjusted under 35 U.S.C. 154(b) by 172 days.

(21) Appl. No.: 17/495,067

(22) Filed: Oct. 6, 2021

(65) Prior Publication Data
US 2022/0106552 A1 Apr. 7, 2022

(30) Foreign Application Priority Data
Oct. 6, 2020 (EP) ..................... 20200195

(51) Int. Cl.
*C12M 3/06* (2006.01)
*C12M 3/00* (2006.01)

(52) U.S. Cl.
CPC ............ *C12M 27/16* (2013.01); *C12M 23/48* (2013.01)

(58) Field of Classification Search
None
See application file for complete search history.

(56) References Cited

U.S. PATENT DOCUMENTS

| 2,829,528 | A | | 4/1958 | Hulick, Jr. | |
|---|---|---|---|---|---|
| 5,060,151 | A | * | 10/1991 | Mikyska | B01F 35/212 |
| | | | | | 318/260 |
| 2008/0299652 | A1 | | 12/2008 | Owen et al. | |
| 2009/0233334 | A1 | * | 9/2009 | Hildinger | C12P 21/02 |
| | | | | | 435/235.1 |
| 2010/0330663 | A1 | * | 12/2010 | Baumfalk | C12M 23/50 |
| | | | | | 435/303.3 |
| 2021/0395663 | A1 | * | 12/2021 | Zhang | C12M 27/16 |

FOREIGN PATENT DOCUMENTS

| CN | 102807953 | A | | 12/2012 |
|---|---|---|---|---|
| CN | 104280286 | A | | 1/2015 |
| EP | 1854871 | A1 | | 11/2007 |
| KR | 20130081516 | A | * | 7/2013 |

OTHER PUBLICATIONS

Document entitled Shaker, machine translation of KR 20130081516 provided by Clarivate (Year: 2013) (Year: 2013).*
"Orbital shaker-incubators" <https://www.gaiascience.com.my/uploads/catalogs/GSM_GrantInstrument_ES20_Datasheet.pdf>, archived at Wayback Machine Aug. 20, 2018 (Year: 2018).*
Extended European Search Report, issued by the European Patent Office, regarding corresponding patent application Serial No. 20200195.4; dated Mar. 19, 2021; 7 pages.

* cited by examiner

*Primary Examiner* — Holly Kipouros
(74) *Attorney, Agent, or Firm* — GREENBERG TRAURIG, LLP

(57) ABSTRACT

It is described an orbital incubator shaker, which comprises an incubator housing (1) defining an incubation chamber (2), and an orbital shaker (3) configured to shake a shaking table (4). The orbital shaker (3) comprises a rotary direct drive motor (7, 8, 9, 10) comprising a stator (7, 8) and a rotor (9, 10) comprising a rotor shaft (9), and an eccentric bearing unit (11, 12, 14) mounted on the rotor shaft (9). The stator (7, 8) is located outside the incubation chamber (2) and the rotor shaft (9) extends from a space (22) outside the incubation chamber (2) towards the incubation chamber (2).

14 Claims, 1 Drawing Sheet

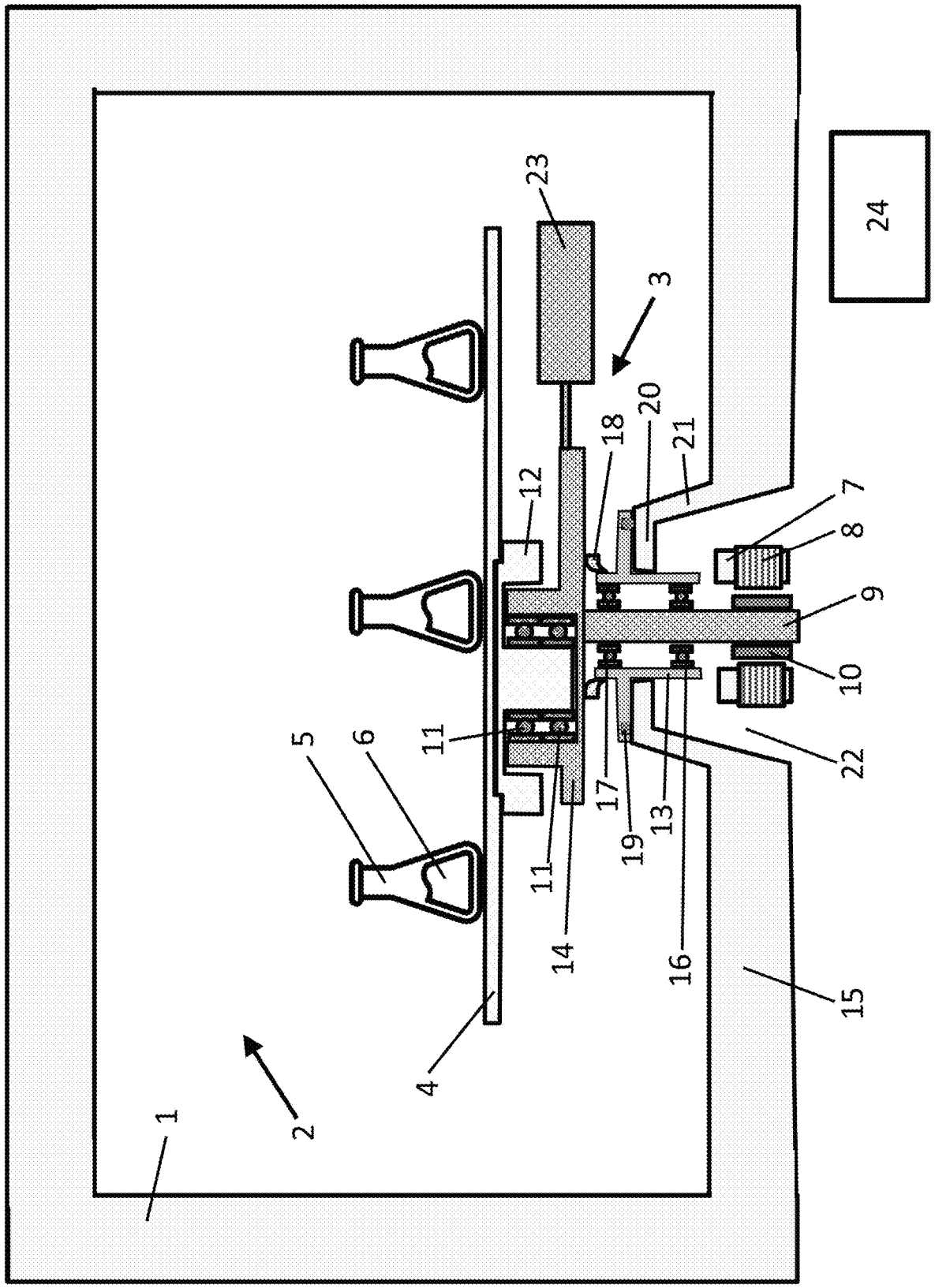

INCUBATOR WITH ORBITAL SHAKER

This application claims priority to European patent application Serial No.: 20200195.4, filed on Oct. 6, 2020; and claims priority to German patent application Serial No.: 20 2020 105 719.7, filed on Oct. 6, 2020; the entireties of which are incorporated herein by reference.

TECHNICAL FIELD

The present disclosure relates to orbital incubator shakers, in particular, devices that have functions of an incubator and an orbital shaker.

BACKGROUND

Known orbital shakers are used in laboratory environments to agitate assays or test samples with orbital motion. Orbital incubator shakers include an incubation chamber for keeping biological materials during the agitation at predetermined environmental conditions. Such known orbital incubator shakers provide a wide range of capabilities to meet specific growth requirements by controlling a variety of environmental parameters inside the incubation chamber, such as temperature, relative humidity, and carbon dioxide concentration.

All known orbital incubator shakers, however, have certain drawbacks, which prevent optimal usage of a shaking device inside an incubator.

For example, document US 2010/0330663 A1 concerns an incubator with a shaker device. The incubator comprises an incubation chamber for cultivating cells and an adjacent device chamber. A part of the shaker device including a shaking table, a drive arm, a drive shaft and eccentric rotary joints is located inside the incubation chamber, whereas another part of the shaker device including a motor and a drive belt is located in the adjacent device chamber. A removable base plate carrying the entire drive assembly separates the incubation chamber from the device chamber. A seal is provided between the base plate and the bottom of the incubation chamber. The seal and the drive belt are wearing parts which have to be exchanged regularly. By removing the base plate, the drive belt and the seal can be accessed and replaced. However, regular replacement of the seal and the drive belt requires relatively high maintenance efforts. Moreover, the structure of the removable base plate carrying the entire drive assembly is largely space-consuming.

Document EP 1 626 082 B1 concerns a shaking system for a cell culture incubator. The incubator comprises an incubation chamber and a device chamber below the incubation chamber. In the device chamber, a motor and a drive belt for rotating an axis, which performs eccentric movements in a horizontal plane, is located. At the free end of the axis, a shaking table for holding cell culture vessels is provided. In order to enable a shaking movement, a sealing between the incubation chamber and the device chamber is made as an elastic bellows type sealing. However, contamination can get from the device chamber into the incubation chamber due to cracks that may occur over time due the motion of the elastic bellows type sealing. Thus, regular replacement of the seal and the drive belt requires relatively high maintenance efforts.

Moreover, the motor and the drive belt are largely space-consuming.

SUMMARY

The present disclosure provides an orbital incubator shaker which overcomes the above explained problems.

According to an aspect, there is provided an orbital incubator shaker comprising an incubator housing defining an incubation chamber, and an orbital shaker configured to shake a shaking table, wherein the orbital shaker comprises a rotary direct drive motor comprising a stator and a rotor comprising a rotor shaft, and an eccentric bearing unit mounted on the rotor shaft.

The incubation chamber may be a kind of closed or closable chamber that enables keeping biological materials during agitation at predetermined environmental conditions. For example, the incubation chamber may be used for mammalian cell culturing. The shaking table may be placed in a fixed manner on the eccentric bearing unit. On the shaking table, a plurality of containers, for example, Erlenmeyer flasks, storing biological material may be releasable fixed and agitated.

The eccentric bearing unit may guide the shaking table to be moved in elliptical orbits, in particular, in varying elliptical orbits. For this, the eccentric bearing unit may comprise closed ball bearings. The eccentric bearing unit may also comprise a mechanical guidance to provide the orbital motion with forced rotation. The eccentric bearing unit may be mounted in a fixed manner to the rotor shaft. It is also possible that the location of the eccentric bearing unit on the rotor shaft can be changed to different positions so that the shaking diameter of the orbital motions may be changed. For this, mechanical means for shifting and fixing the position of the eccentric bearing unit on the rotor shaft may be provided.

The rotary direct drive motor may be a torque motor. The stator of the direct drive motor may surround the rotor and may comprise direct current electro-magnets and sensors, and the rotor may comprise at an outer circumferential surface permanent magnets. The electro-magnets of the stator may by switched by a control unit (e.g., a microprocessor) depending on the position of the rotor determined by the sensors. Since the rotary direct drive motor does not comprise any mechanical power transfer means (for example, a belt), there is close to no abrasion. Moreover, rotary direct drive motors provide the advantages of low noise, low power consumption, and low heat generation. Furthermore, since the motor speed of the rotary direct drive motor is the same as the shaking speed of the shaking table, the control unit may easily change the shaking speed of the shaking table. Specifically, the rotary direct drive motor ensures a high performing rotary movement regarding shaking speed (rpm) and load (kg) of the shaking table.

Moreover, due to the structure of the eccentric bearing unit being mounted on the rotor shaft of the rotary direct drive motor, a compact design with a relatively small height difference between the rotary direct drive motor and the shaking table is provided, which helps to prevent strong vibrations at the shaking table.

In order to increase the size of the incubation chamber, the stator may be located outside the incubation chamber and the rotor shaft may extend from outside the incubation chamber towards the incubation chamber. Specifically, the rotor shaft may extend from outside the incubation chamber into an area of the incubation chamber.

Furthermore, the rotary direct drive motor may be located outside the incubation chamber and the rotor shaft may extend from outside the incubation chamber towards the incubation chamber.

According to one aspect, the incubator housing comprises at its base a base element extending into the incubation chamber. Thus, the base of the incubator housing may not only be a base plate, but may be a base plate with a base element having a convex surface facing the incubation chamber. Within the base element, an opening for fixing the orbital shaker may be present. Thus, an orbital incubator shaker having a compact design may be provided.

The base element may comprise a horizontal base element and an extension base element, which extends between the base and the horizontal base element. Moreover, the horizontal base element may comprise the opening at which the orbital shaker may be mounted.

In order to provide a compact and stable design of the orbital incubator shaker, the stator may be located in a space outside the incubation chamber which is defined by the base element. In this case, the rotor shaft may extend from the space through the opening provided in the base element (i.e., the horizontal base element) towards the incubation chamber.

Furthermore, the rotary direct drive motor may be located in a space outside the incubation chamber which is defined by the base element.

The orbital incubator shaker may further comprise a bushing mounted to the base element and configured to fix the orbital shaker to the base element of the incubator housing. The bushing may be mounted at the opening of the base element (i.e., the horizontal base element). Thus, even when shaking heavy loads, strong vibrations at the shaking table may be prevented.

The orbital incubator shaker may further comprise a first bearing provided between the rotor shaft and the bushing, and a second bearing provided between the rotor shaft and the bushing, wherein the second bearing is located at a location of the bushing that is extended into the incubation chamber and the first bearing is located outside the incubation chamber. The first and second bearings may be ball bearings. By means of the first and second bearings, the rotor shaft may be supported at the bushing and rotate within the bushing. This arrangement of the first and second bearings further helps to prevent strong vibrations at the shaking table.

In order to seal the inside of the incubation chamber from the outside of the incubation chamber and the stator, the first bearing and/or the second bearing may be sealed ball bearings. Each ball bearing may comprise a bearing isolator having a labyrinth seal design to enable sealing of the stator from the incubation chamber and additionally prevent lubricant leakage from the bearing.

To further seal the inside of the incubation chamber from the outside of the incubation chamber, the rotor and/or the stator, a dynamic seal may be provided between the bushing and the eccentric bearing unit. Thus, the bushing, the dynamic seal, and the eccentric bearing unit may be configured to seal the stator and the rotor from the incubation chamber. For this, the incubator housing, the bushing, the dynamic seal, and the eccentric bearing unit may seal the incubation chamber. The dynamic seal may be configured such that it retains or separates moisture and fluids, keeps out contaminants, and contains temperature and climate in the incubation chamber. Moreover, it may create a barrier between moving and stationary surfaces in the orbital shaker. In particular, although the rotary direct drive motor only generates low heat, the dynamic seal helps to keep the temperature in the incubation chamber. The dynamic seal may be a contact seal bearing the seal against a mating surface under positive pressure, or a clearance seal operating with positive clearance so that there is no rubbing contact.

In particular, to prevent a loss of cell cultures due to contamination, it is important to efficiently clean, disinfect and decontaminate the incubation chamber, i.e., all surfaces within the incubation chamber. For example, this is essential for a Good-Manufacturing-Practice—(GMP) compliant cell cultivation. Moreover, a precisely controlled climate in the incubation chamber is necessary to maintain optimal cell culture conditions. To fulfil these requirements, the stator and the rotor may be fully sealed from the incubation chamber. Thus, on the one hand, the sealing of the stator and the rotor from the incubation chamber by means of the incubator housing, the bushing, the dynamic seal, and the eccentric bearing unit helps to provide surfaces within the incubation chamber that can be easily cleaned, disinfected and decontaminated. On the other hand, the sealing of the heat-generating rotor and stator from the incubation chamber helps to facilitate controlling the temperature in the incubation chamber.

The dynamic seal may comprise a lip seal mounted on the bushing. The lip seal may be a flexible lip and may point towards the incubation chamber to ensure keeping the incubation chamber clean and uncontaminated. The dynamic seal may further comprise a spring helping to keep the lip seal in contact with the eccentric bearing unit, e.g., a bearing base of the eccentric bearing unit. Preferably, the lip seal is an U.S. Food and Drug Administration—(FDA) approved tight-seal.

To improve the sealing of the stator from the incubation chamber, an O-ring may be provided, which seals the bushing to the incubator housing. The O-ring may be provided at the bushing and seal the bushing to the horizontal base element of the base element.

To provide an orbital incubator shaker having a compact design which at the same time enables a stable shaking, the stator may be located on and/or above a horizontal plane defined by the base of the incubator housing. Thus, for placing the orbital incubator shaker on the ground, the base, or an additional ground plate provided under the base, may be placed on the ground.

Furthermore, the rotary direct drive motor may be located on and/or above a horizontal plane defined by the base of the incubator housing.

To compensate centrifugal forces created by liquid masses stored in containers fixed on the shaking table, the orbital shaker may further comprise an adjustable counterweight mounted within the incubation chamber to the eccentric bearing unit. For example, the adjustable counterweight may be screwed to a bearing base of the eccentric bearing unit. The counterweight allows manual calibration in case of imbalance situations so that liquid stored in the containers may be shaken at high speed. The counterweight may also be adjusted in accordance with a shifting of the location of the eccentric bearing on the rotor shaft.

Preferably, a diameter of the orbital movement of the shaking table may be between 19 and 50 mm. Further preferably, the rotation speed of the shaking table may be between 80 and 200 rpm with a maximum rotation speed of 400 rpm. Further preferably, the load to be shaken may be up to 25 kg.

To ensure corrosion resistance, chemical resistance and easy cleaning of all surfaces within the incubation chamber, the bushing, the eccentric bearing unit with the mounted counterweight, the shaking table and/or an inner surface of the incubation chamber is made of stainless steel.

On the shaking table, 153 pcs. to 5 pcs. Erlenmeyer flasks, which may be up to 365 mm high and may contain between 10 ml and 3000 ml of liquid, may be fixed in a releasable manner. To absorb respective lever forces during shaking, the eccentric bearing unit may comprise a bearing base mounted on the rotor shaft, two sealed bearings that are stacked above each other at the bearing base, and an eccentric supported by the two sealed bearings. In addition, the shaking table may be mechanically guided so that it performs an orbital movement instead of a circular movement. Alternatively, such stable movement may be obtained with two pairs of leaf springs.

BRIEF DESCRIPTION OF THE DRAWING

FIG. 1 is a cross-sectional diagram schematically illustrating an embodiment of an orbital incubator shaker.

DETAILED DESCRIPTION

Generally, all terms used herein are to be interpreted according to their ordinary meaning in the relevant technical field, unless a different meaning is clearly given and/or is implied from the context in which it is used. All references to a/an/the element, apparatus, component, means, step, etc. are to be interpreted openly as referring to at least one instance of the element, apparatus, component, means, step, etc., unless explicitly stated otherwise. Any feature of any of the embodiments disclosed herein may be applied to any other embodiment, wherever appropriate. Likewise, any advantage of any of the embodiments may apply to any other embodiments, and vice versa. Other objectives, features and advantages of the enclosed embodiments will be apparent from the following description.

Some of the embodiments contemplated herein will now be described more fully with reference to the accompanying drawings. Other embodiments, however, are contained within the scope of the subject matter disclosed herein, the disclosed subject matter should not be construed as limited to only the embodiments set forth herein. Rather, these embodiments are provided by way of example to convey the scope of the subject matter to those skilled in the art.

FIG. 1 is a cross-sectional diagram schematically illustrating an embodiment of an orbital incubator shaker. The orbital incubator shaker comprises an incubator having an incubator housing 1 defining an incubation chamber 2 and an orbital shaker 3.

The incubator may comprise further elements for operating the incubator which are not shown in FIG. 1, for example, a separate heating device for heating the air, fans that suck air into the incubation chamber 2 and other arrangements forcing the air to circulate throughout the whole chamber, temperature and climate control means, a user interface, etc.

The incubator housing 1 comprises at its bottom a base 15, which may be placed on the ground. At a central location of the base 15, a base element 20, 21 extending into the incubation chamber 2 is provided. The base element 20, 21 comprises a horizontal base element 20 and an extension base element 21, which extends between the base 15 and the horizontal base element 20. Other convex shapes of the base element 20, 21 are possible. At the center of the horizontal base element 20, an opening is provided. When seen from above, the opening has a circular shape. The horizontal base element 20, the extension base element 21 and a plane corresponding to the base 15 define a space 22 beneath the incubation chamber 2.

Additionally, a base plate (not shown in FIG. 1) may be foreseen below the base 15, which closes the space 22 and on which the orbital incubator shaker may be placed on the ground.

On the orbital shaker 3, a shaking table 4 is releasable fixed. On top of the shaking table 4, three Erlenmeyer flasks 5 are releasable fixed. Within each Erlenmeyer flask 5, a biological liquid 6 is stored. When the shaking table 4 is shaken by the orbital shaker 3, the biological liquid 6 is shaken.

The orbital shaker 3 comprises a rotary direct drive motor 7, 8, 9, 10, two ball bearings 16, 17, a bushing 13, a lip seal 18, an eccentric bearing unit 11, 12, 14, and an adjustable counterweight 23. FIG. 1 further shows a control unit 24 which controls the rotary direct drive motor 7, 8, 9, 10.

The rotary direct drive motor 7, 8, 9 and 10 comprises a stator 7, 8, and a rotor 9, 10. The stator 7, 8 comprises a plurality of axis elements 7 around which magnetic coils 8 are wound, and which act as electro-magnets. The stator 7, 8 surrounds the rotor 9, 10. The rotor 9, 10 comprises a rotor shaft 9 and a plurality of permanent magnets 10 disposed at an outer circumferential surface of the rotor shaft 9. The rotor shaft 9 extends from the space 22 towards the incubation chamber 2. Furthermore, sensors (not shown in FIG. 1) for determining the position of the rotor 9, 10 are provided. Depending on the determined positions of the rotor 9, 10, the control unit 24 controls electric currents supplied to the magnetic coils 8 in order to rotate the rotor 9, 10. Further necessary elements of the rotary direct drive motor 7, 8, 9 and 10, like electric cables and connections to the control unit 24 are not shown in the schematic illustration of FIG. 1.

For fixing the orbital shaker 3 to the incubator housing 1, the bushing 13 is provided at an inner wall of the opening of the horizontal base element 20 and on a surface of the horizontal base element 20 facing the incubation chamber 2. The bushing 13 has a cross sectional double-T-shape extending from the space 22 through the opening into the incubation chamber 2. The bushing 13 may be screwed to the horizontal base element 20. For sealing the bushing 13 to the horizontal base element 20 of the incubator housing 1, an O-ring 19 is foreseen at the bushing 13. The O-ring 19 is in contact with the surface of the horizontal base element 20 facing the incubation chamber 2.

For supporting the rotor shaft 9 at the bushing 13, the first ball bearing 16 is provided at a lower end of the bushing 13 between the bushing 13 and the rotor shaft 9, and the second ball bearing 17 is provided at an upper end of the bushing 13 between the bushing 13 and the rotor shaft 9. Thus, the rotor shaft 9 together with the permanent magnets 10 can be rotated by the stator 7, 8. Preferably, the first and second ball bearings 16, 17 are sealed ball bearings.

On top of the rotor shaft 9, the eccentric bearing unit 11, 12, 14 is mounted. The eccentric bearing unit 11, 12, 14 comprises a bearing base 14, two ball bearings 11 stacked upon each other, and an eccentric 12. The two ball bearings 11 are sealed ball bearings.

The bearing base 14 comprises a tray-shaped part. The two ball bearings 11 are mounted inside the tray-shaped part of the bearing base 14. In the cross-sectional view of FIG. 1, it can be seen that the tray-shaped part is located apart from the center of the bearing base 14.

The eccentric 12 comprises an inner shaft having a cylindrical shape which is supported inside the two ball bearings 11 so that it may be rotated. Additionally, the eccentric 12 mechanically guides the shaking table 4 such that it moves in orbital motions. The eccentric 12 covers an upper part of the bearing base 14, i.e., the tray-shaped part of the bearing base 14, and the two ball bearings 11. On top of the eccentric 12, the shaking table 4 is placed. The shaking table 4 may be releasable fixed to the eccentric 12.

In another embodiment (not shown in FIG. 1), mechanics may be provided at the eccentric 12, which enable the eccentric 12 to be moved to and locked at different positions to the left and/or right in the horizontal plane. Thereby, the shaking diameter of the orbital motions may be changed.

Attached to the bearing base 14 (for example, screwed to the bearing base 14) is the counterweight 23. The counterweight 23 is adjustable in that its distance from the bearing base 14 may be manually adjusted in order to counter imbalances due to heavy loads 5, 6 placed on the shaking table 4. The counterweight 23 may also be adjusted at the same time when the eccentric 12 is moved to and locked at different positions to the left and/or right in the horizontal plane.

The lip seal 18 provides a sealing between the bushing 13 and the bearing base 14. The lip seal 18 is a flexible FDA-approved tight-seal and is mounted on the bushing 13. The lip seal 18 points towards the bearing base 14, and helps to keep the incubation chamber 2 clean and uncontaminated.

The bushing 13, the O-ring 19, the lip seal 18 and the bearing base 14 seal the stator 7, 8 and the rotor 9, 10 from the incubation chamber 2. Since the first and second ball bearings 16, 17 are sealed ball bearings, in addition to the lip seal 18, second and third sealing layers for sealing the stator 7, 8 from the incubation chamber 2 can be provided.

In another embodiment (not shown in FIG. 1), the lip seal 18 is omitted and at least the second ball bearing 17 is a sealed ball bearing. In this case, the bushing 13, the O-ring 19, and the second ball bearing 17 seal the stator 7, 8 from the incubation chamber 2. This embodiment has the advantage that no moving part of the orbital shaker 3 penetrates into the incubation chamber 2.

In order to facilitate cleaning, disinfection and decontamination of the orbital incubator shaker, the inner surface of the incubator housing 1, the bushing 13, the eccentric bearing unit 11, 12, 14 with attached counterweight 23, the shaking table 4 may be made of stainless steel. Moreover, the outer surface of the incubator housing 1 or the entire incubator housing 1 may be made of stainless steel. Additionally, the surfaces of the orbital shaker 3 facing the incubation chamber 2 may be designed such that no hidden vaults or dead spaces are present. Specifically, all connections of the elements of the orbital shaker 3 are not only covered but also sealed. In particular, the orbital shaker 3 is designed to comply with the norm ISO 14159:2002 "Safety of machinery—Hygiene requirements for the design of machinery" such that all parts inside the incubation chamber 2 are accessible for cleaning and disinfection.

The above described embodiments provide some or all of the following advantages:

The orbital incubator shaker is designed in accordance with known hygienic design principles. The choice of material, surface quality and the absence of cavities allow for easy and thorough cleaning, disinfection and decontamination of the orbital incubator shaker, which allows GMP-compliant cell cultivation.

The encapsulation of the orbital shaker 3 protects the rotary direct drive motor 7, 8, 9 and 10 and all electronic parts from moisture and microbial contamination as well as from chemicals used for cleaning, disinfection and decontamination of the incubation chamber 2.

Except the lip seal 18, no rotating part penetrates into the incubation chamber 2.

The orbital shaker 3 has a simple, space-saving and clean design, and the orbital shaker 3 may be easily dismantled, replaced and/or repaired.

The direct drive motor 7, 8, 9 and 10 has a low net energy consumption leading to low heat emission.

A small height difference between the direct drive motor 7, 8, 9 and 10 and the load 5, 6 leads to reduced vibrations.

What is claimed is:

1. An orbital incubator shaker, comprising:
    an incubator housing defining an incubation chamber,
        wherein the incubator housing comprises at its base a base element extending into the incubation chamber;
    an orbital shaker configured to shake a shaking table,
        wherein the orbital shaker comprises:
            a rotary direct drive motor comprising a stator and a rotor comprising a rotor shaft, and
            an eccentric bearing unit mounted on the rotor shaft;
    a bushing mounted to the base element and configured to fix the orbital shaker to the base element;
    a first bearing provided between the rotor shaft and the bushing,
        wherein the first bearing is located outside the incubation chamber; and
    a second bearing provided between the rotor shaft and the bushing;
        wherein the second bearing is located at a location of the bushing that is extended into the incubation chamber.

2. The orbital incubator shaker of claim 1, wherein the stator is located outside the incubation chamber and the rotor shaft extends from outside the incubation chamber towards the incubation chamber.

3. The orbital incubator shaker of claim 1, wherein the base element comprises a horizontal base element and an extension base element, which extends between the base element and the horizontal base element.

4. The orbital incubator shaker of claim 1, wherein the stator is located in a space outside the incubation chamber which is defined by the base element.

5. The orbital incubator shaker of claim 1, wherein at least one of the first bearing and the second bearing is a sealed ball bearing.

6. The orbital incubator shaker of claim 1, wherein the orbital shaker further comprises:
    a dynamic seal provided between the bushing and the eccentric bearing unit,
        wherein the bushing, the dynamic seal, and the eccentric bearing unit are configured to seal the stator and the rotor from the incubation chamber.

7. The orbital incubator shaker of claim 6, wherein the dynamic seal comprises a lip seal mounted on the bushing.

8. The orbital incubator shaker of claim 1, further comprising:
    an O-ring configured to seal the bushing to the incubator housing.

9. The orbital incubator shaker of claim 1, wherein the stator is located on or above a horizontal plane defined by a base of the incubator housing.

10. The orbital incubator shaker of claim 1, wherein the eccentric bearing unit comprises:
    a bearing base mounted on the rotor shaft,
    two sealed bearings that are stacked above each other at the bearing base, and
    an eccentric supported by the two sealed bearings.

11. The orbital incubator shaker of claim 1, further comprising:
    an adjustable counterweight mounted within the incubation chamber to the eccentric bearing unit.

12. The orbital incubator shaker of claim 11, wherein at least one of the bushing, the eccentric bearing unit with the adjustable counterweight, the shaking table and an inner surface of the incubation chamber is made of stainless steel.

13. An orbital incubator shaker, comprising:
    an incubator housing defining an incubation chamber, wherein the incubator housing comprises at its base a base element extending into the incubation chamber;
an orbital shaker configured to shake a shaking table, wherein the orbital shaker comprises:
    a rotary direct drive motor comprising a stator and a rotor comprising a rotor shaft, and
    an eccentric bearing unit mounted on the rotor shaft;
a bushing mounted to the base element and configured to fix the orbital shaker to the base element; and
a dynamic seal provided between the bushing and the eccentric bearing unit,
    wherein the bushing, the dynamic seal, and the eccentric bearing unit are configured to seal the stator and the rotor from the incubation chamber.

14. An orbital incubator shaker, comprising:
an incubator housing defining an incubation chamber; and
an orbital shaker configured to shake a shaking table, wherein the orbital shaker comprises:
    a rotary direct drive motor comprising a stator and a rotor comprising a rotor shaft, and
    an eccentric bearing unit mounted on the rotor shaft;
wherein the eccentric bearing unit comprises:
  a bearing base mounted on the rotor shaft;
  two sealed bearings that are stacked above each other at the bearing base; and
  an eccentric supported by the two sealed bearings.

\* \* \* \* \*